US00PP11334P

United States Patent [19]

Dümmen

[11] Patent Number: Plant 11,334

[45] Date of Patent: Apr. 11, 2000

[54] POINSETTIA PLANT NAMED 'DUEWI'

[75] Inventor: Marga Dümmen, Rheinberg, Germany

[73] Assignee: Dummen Jungpflanzenkulturen, Rheinberg, Germany

[21] Appl. No.: 09/105,363

[22] Filed: Jun. 26, 1998

[51] Int. Cl.[7] ..... A01H 5/00

[52] U.S. Cl. ..... Plt./307

[58] Field of Search ..... Plt./307

[56] References Cited

U.S. PATENT DOCUMENTS

P.P. 7,874 5/1992 Fruehwirth ..... Plt./307

P.P. 8,250 6/1993 Trees ..... Plt./307

P.P. 9,632 8/1996 Trees ..... Plt./307

P.P. 9,854 4/1997 Dümmen ..... Plt./307

*Primary Examiner*—Howard J. Locker

*Assistant Examiner*—Kent L. Bell

*Attorney, Agent, or Firm*—C. A. Whealy

[57] ABSTRACT

A new and distinct variety of Poinsettia plant named 'Duewi', characterized by its dark red flower bracts; flower bracts held horizontal to stem axis; very dark green foliage; freely branching plant habit; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Duewi'.

The new Poinsettia is a product of a planned breeding program conducted by the Inventor in Rheinberg, Germany. The objective of the breeding program was to develop new Poinsettias that are freely branching; flower early; have desirable flower bract and leaf color; and have excellent postproduction longevity.

The new Poinsettia originated from a cross made by the Inventor of the proprietary Poinsettia selection identified as code number F-1 as the male or pollen parent with a proprietary Poinsettia selection identified as code number M-115 as the female or seed parent. 'Duewi' was discovered and selected in 1994 by the Inventor as a single flowering plant within the progeny of the stated cross in a controlled environment in Rheinberg, Germany.

Asexual reproduction of the new Poinsettia by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duewi'. These characteristics in combination distinguish 'Duewi' as a new and distinct variety:

1. Dark red flower bracts.
2. Flower bracts held horizontal to stem axis.
3. Very dark green foliage.
4. Freely branching plant habit.
5. Excellent postproduction longevity.

In side-by-side comparisons conducted by the Inventor in Rheinberg, Germany, plants of the new Poinsettia are more freely branching, more vigorous and have a darker red bract color than plants of the male parent, selection number F-1. Compared to plants of the female parent, selection M-115, plants of the new Poinsettia are more vigorous, have darker green leaves and brighter red bract color.

Plants of the new Poinsettia can be compared to plants of the Poinsettia cultivar 'Duedeluxe' (disclosed in U.S. Plant patent application Ser. No. 09/105,362). However, in side-by-side comparisons conducted by the Inventor in Rheinberg, Germany, plants of the new Poinsettia flower slightly later, bracts are more horizontal (less upright), and leaves tend to be less deeply lobed than bracts and leaves of plants of the cultivar 'Duedeluxe'.

Plants of the new Poinsettia can be compared to plants of the cultivar 'Fiscor' (disclosed in U.S. Plant Pat. No. 9,364). However, in side-by-side comparisons conducted by the Inventor in Rheinberg, Germany, bracts of plants of the new Poinsettia are more intense and darker red in color than plants of the cultivar 'Fiscor'. In addition, plants of the new Poinsettia are less compact, but not as broad as plants of the cultivar 'Fiscor'.

BRIEF DESCRIPTION OF THE PHOTOGRAPH

The accompanying colored photograph illustrates the overall appearance of the new Poinsettia, showing the colors as true as it is reasonably possible to obtain in a colored reproduction of this type. The photograph comprises a top perspective view of a typical plant of 'Duewi' that was pinched and grown in a 15-cm container. Bract and leaf colors in the photograph may appear lighter than the actual colors due to light reflectance.

DETAILED BOTANICAL DESCRIPTION

Plants of 'Duewi' have not been observed under all possible environmental conditions. The phenotype may vary somewhat with variations in environment such as temperature, daylength and light intensity, without, however, any variance in genotype. The following observations and measurements describe plants grown in Rheinberg, Germany, under commerical practice in a glass-covered greenhouse with day temperatures about 22° C., night temperatures about 18° C. and light levels about 30,000 to 40,000 lux. Plants were grown in 15-cm pots, pinched one time, and flowered under long nyctoperiods.

In the following description, color references are made to The Royal Horticultural Society Colour Chart except where general terms of ordinary dictionary significance are used.

Botanical classification: *Euphorbia pulcherrima* Willd. 'Duewi'.

Parentage:

*Male, or pollen, parent.*—Proprietary selection of *Euphorbia pulcherrima* Willd. identified as code number F-1.

*Female, or seed, parent.*—Proprietary selection of *Euphorbia pulcherrima* Willd. identified as code number M-115.

Propagation:

*Type cutting.*—Terminal cuttings.

*Time to initiate roots.*—Summer: About 10 days at 22° C. Winter: About 12 days at 22° C.

*Time to develop roots.*—Summer: About 21 days at 22° C. Winter: About 28 days at 22° C.

*Rooting habit.*—Thick, freely branching.

Plant description:

*Plant form.*—Inverted triangle, top of plant rounded to flat.

*Growth habit.*—Freely branching and upright. Branching is enhanced by removing the shoot apex. Moderate to rapid growth rate and vigorous. Suitable for 10 to 16-cm containers.

*Plant height.*—About 25 cm.

*Crop time.*—From rooted cuttings to a flowering plant in a 15-cm container, about 11.5 weeks are required.

*Foliage description.*—Quantity of leaves: About 85 per flowering plant. Length: About 9.5 cm. Width: About 7 cm. Shape: Deltoid, palmatifid. Apex: Apiculate. Base: Acute. Margin: Entire. Texture: Velvety, glabrous. Color: Young foliage, upper surface: 136A. Young foliage, lower surface: 139B. Mature foliage, upper surface: 136A. Mature foliage, lower surface: 139B. Venation, upper surface: 136C. Venation, lower surface: 143B. Petiole: Length: About 5.25 cm. Color: 136A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Time to flower.*—About 8.5 weeks under long nyctoperiod conditions.

*Quantity of inflorescences.*—One per lateral branch, usually about seven per plant.

*Inflorescence size.*—Diameter: About 24 cm. Height (depth): About 3 cm.

*Flower bracts.*—Orientation: Mostly upright. Quantity of flower bracts per inflorescence: About 12 per inflorescence. Length: About 9.5 cm. Width: About 5.9 cm. Shape: Roughly ovate. Apex: Apiculate. Margin: Entire. Base: Acute to obtuse. Texture: Smooth, satiny. Color: Mature, upper surface: 46A. Mature, lower surface: 46C. After senescence, upper surface. 46D.

*Cyathia.*—Quantity: Usually about nine per corymb. Diameter of cyathia cluster: About 3 cm. Length: About 9 mm. Width: About 4 mm. Color: Immature: 143C. Mature: 143A. Peduncle: Length: About 1.75 cm. Aspect: Erect. Color: 53A. Stamens: Stamen number: About nine per cyathium. Anther size: About 1 mm. Anther shape: Rounded. Pistils: Pistil number: Typically one per cyathium. Stigma shape: Trilobate. Stigma color: 46A. Style length: About 2.5 mm. Ovary number: Three. Nectaries: Usually one and sometimes two per cyathium.

Disease resistance: No fungal, bacterial nor viral problems observed on plants grown under commercial conditions.

Postproduction Longevity: Generally plants maintain good substance and bract color for about five to six weeks under interior conditions.

It is claimed:

1. A new and distinct variety of Poinsettia plant named 'Duewi', as illustrated and described.

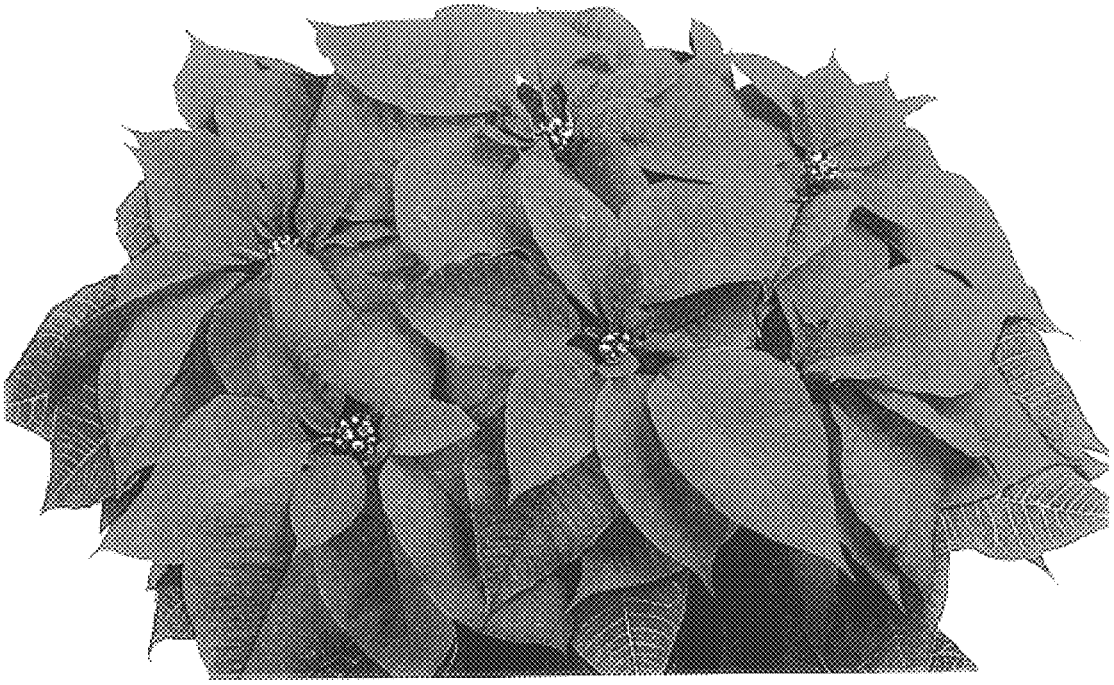

* * * * *